(12) United States Patent
Ishikawa et al.

(10) Patent No.: US 6,254,548 B1
(45) Date of Patent: Jul. 3, 2001

(54) INTERNAL THERMOMETER

(75) Inventors: Akira Ishikawa, Royce City; Nabuo Takeda, Richardson; Suzanne I. Ahn, Dallas, all of TX (US); Samuel S. Ahn, Los Angeles, CA (US); Steven R. Hays, Dallas, TX (US); F. Andrew Gaffney, Nashville, TN (US)

(73) Assignee: Ball Semiconductor, Inc., Allen, TX (US)

( * ) Notice: Subject to any disclaimer, the term of this patent is extended or adjusted under 35 U.S.C. 154(b) by 0 days.

(21) Appl. No.: 09/448,638

(22) Filed: Nov. 24, 1999

Related U.S. Application Data
(60) Provisional application No. 60/110,041, filed on Nov. 25, 1998.

(51) Int. Cl.[7] .................................................. A61B 5/00
(52) U.S. Cl. .......................................... 600/549; 600/486
(58) Field of Search ................................ 600/549, 555, 600/486

(56) References Cited

U.S. PATENT DOCUMENTS

| | | | |
|---|---|---|---|
| 3,971,362 | * | 7/1976 | Pope et al. ............................ 600/302 |
| 5,446,452 | * | 8/1995 | Litton ................................ 340/870.17 |
| 5,697,384 | * | 12/1997 | Miyawaki et al. .................... 128/899 |
| 5,724,030 | * | 3/1998 | Urbas et al. ..................... 340/870.17 |
| 5,984,875 | * | 11/1999 | Bruno .................................. 600/549 |
| 6,015,390 | * | 6/1998 | Krag ..................................... 600/549 |

\* cited by examiner

*Primary Examiner*—Cary O'Connor
*Assistant Examiner*—Pamela Wingood
(74) *Attorney, Agent, or Firm*—Howison, Chauza, Thoma, Handley & Arnott, L.L.P.

(57) ABSTRACT

A miniature spherical-shaped internal temperature transponder. A temperature sensor (25) is fabricated in a spherical integrated transponder circuit (15) which may be placed in the human body by ingestion, implantation, or injection. In one aspect of the invention, a passive system is disclosed whereby an external monitoring station (13) generates an energy field using a magnetic field generator (19) which is coupled to a power coil (21) of the transponder (15). The power coil (21) passes power to a power regulator (23) to provide regulated power to all transponder (15) circuits. Temperature data obtained by the temperature sensor (25) is passed to a voltage controlled oscillator (27) for conversion into an RF signal. A mixing circuit (31) receives the RF temperature signal and modulates the temperature data signal onto an oscillator frequency from an RF oscillator (29). An RF amplifier (33) receives the modulated RF signal from the mixing circuit (31) and transmits it via an antenna (35) to the external monitor station 13 which is proximate to the transponder (15). The signal is received by an RF receiver (37) and processed using a CPU (39) to extract the measured temperature data, which can then be displayed to the operator on a display (41). The transponder (15) may be powered either by the external electromagnetic radiation source (19) or an internal battery.

11 Claims, 6 Drawing Sheets

INTERNAL THERMOMETER

CROSS-REFERENCE TO RELATED APPLICATIONS

This application claims priority under 35 U.S.C. 119(e) from U.S. Provisional Patent Application Serial No. 60/110,041 filed on Nov. 25, 1998, having the same title as this application.

This application is related to co-pending U.S. patent application Ser. No. 09/323,585 entitled "IMPLANTABLE EPICARDIAL ELECTRODE," filed on Jun. 2, 1999; U.S. Provisional Patent Application Serial No. 60/137,071 entitled "GLUCOSE SENSOR," filed on Jun. 2, 1999; U.S. patent application Ser. No. 09/498,781 entitled "SPHERICALLY-SHAPED BIOMEDICAL IC," filed of even date; U.S. patent application Ser. No. 09/448,642 entitled "MINIATURE SPHERICAL-SHAPED SEMICONDUCTOR WITH TRANSDUCER," filed of even date; U.S. patent application Ser. No. 09/448,638 entitled "INTERNAL THERMOMETER," filed even date; U.S. patent application Ser. No. 09/498,644 entitled "MONITOR FOR INTERVENTIONAL PROCEDURES," filed of even date.

TECHNICAL FIELD OF THE INVENTION

This invention is related generally to the field of clinical temperature monitoring, and more particularly to a method of and system for monitoring temperature with an ingestible or implantable, almost microscopic, temperature transponder, preferably built on a single semiconductor substrate.

BACKGROUND OF THE INVENTION

Typically, a patient's temperature is taken orally, axillary, or rectally. The method chosen is based upon the age and consciousness of the patient. Originally, temperature was measured with a conventional glass and mercury clinical thermometer. Glass and mercury thermometers can be dangerous to use and they require substantial time to reach the patient's actual temperature.

Recently, electronic or digital thermometers have been developed to overcome the shortcomings of conventional glass and mercury clinical thermometers. One type of digital thermometer is a tympanic thermometer, which senses infrared radiation from a patient's ear drum. Tympanic thermometers provide a fast temperature reading, but their accuracy tends not to be as good as conventional clinical thermometers. Another type of digital thermometer includes a temperature sensing probe and circuitry for calculating and displaying the temperature detected by the probe. The probe may be used in the same way as a conventional glass and mercury clinical thermometer to measure oral, axillary, or rectal temperature. The probe type digital thermometers tend to provide accurate temperature readings almost as fast as tympanic thermometers.

Existing clinical thermometers, whether conventional or digital, have certain drawbacks in terms of time and effort on the part of the healthcare professional and inconvenience to the patient. NASA (National Aeronautics and Space Administration) has developed an ingestible thermometer that it uses to monitor the temperature of its astronauts. The NASA thermometer includes a temperature sensor, a transmitter, and a battery encapsulated in a relatively large pill-like structure. The NASA ingestible thermometer transmits the astronaut's temperature periodically to an external receiver. The NASA ingestible thermometer offers certain advantages over conventional thermometers. Temperature is recorded substantially automatically and continuously without inconvenience to monitoring personnel or the subject. However, the NASA ingestible thermometer requires an internal battery, and therefore, is rather large and difficult to swallow, and consequently, nearly impossible for use with children. Moreover, the NASA ingestible thermometer is too expensive to be used in a doctor's office or hospital.

SUMMARY OF THE INVENTION

The present invention disclosed and claimed herein, in one aspect thereof, comprises a method and system for monitoring an internal temperature. According to this aspect, an almost microscopic temperature transponder is placed internally of a body. The transponder may be placed by ingestion, implantation, or injection. The transponder generates an RF signal based upon the temperature of the transponder. The RF signal is received externally of the body and the internal temperature is determined based upon the received RF signal. The transponder is powered either by an external electromagnetic radiation source or an internal battery.

In one aspect, the transponder of the present invention is built on a single semiconductor substrate. Preferably, the semiconductor substrate is substantially spherical in shape. A temperature sensor resides on the substrate. Signal generating circuitry residing on the substrate generates an RF signal corresponding to the temperature sensed by the temperature sensor. Power generating circuitry residing on the substrate powers the temperature sensor and the signal generating circuitry in response to the external electromagnetic signal. The temperature sensor produces a voltage that corresponds to temperature. The temperature sensor can include a thermistor. The temperature sensor is coupled to a voltage controlled oscillator. The voltage controlled oscillator produces a signal, the frequency of which is related to the temperature sensed by the sensor. The signal produced by the voltage controlled oscillator modulates an RF signal generated by RF oscillator circuitry residing on the substrate.

In another aspect, the transponder is built on a cluster of ball elements. The circuitry for generating a temperature dependent RF signal resides on a first substantially spherical semiconductor substrate. The temperature sensor resides on a second substantially spherical substrate coupled to the first substrate. The transponder may by powered either by a substantially spherical battery ball coupled to at least one of the first or second substrates, or by circuitry for generating power in response to an external electromagnetic signal. The power generating circuitry may reside in one of the first or second substrates. Alternatively, the power generating circuitry may reside on a third substantially spherical semiconductor substrate coupled to at least one of the first or second substrates.

The transponder of the disclosed architecture is encapsulated in a biologically inert coating. In the ingestible embodiment, the transponder is small enough to be ingested easily, but not so small as to be absorbed by phagocytosis through the microvilli in the lining of the digestive tract. Preferably, the transponder of the present invention is approximately one millimeter in diameter.

BRIEF DESCRIPTION OF THE DRAWINGS

For a more complete understanding of the present invention and the advantages thereof, reference is now made to the following description taken in conjunction with the accompanying Drawings in which.

DETAILED DESCRIPTION OF THE INVENTION

The spherical geometry of the semiconductor ball devices disclosed herein offer a number of advantages compared to conventional semiconductor devices having a planar or two-dimensional geometry. By way of illustration, a few of these advantages include the following: a spherical device has a smooth, rounded shape which is easily implanted or injected into a biological medium and which passes easily through a biological medium if necessary in a particular application. Further, the large surface area of a spherical device relative to its overall dimensions provides for the maximum of surface area devoted to functional regions in contact with the biological medium such as transducers and other circuitry. Further, the spherical device permits disposition of transducers aligned on all three geometric axes for maximum transducer function on a single device.

Figure 1:
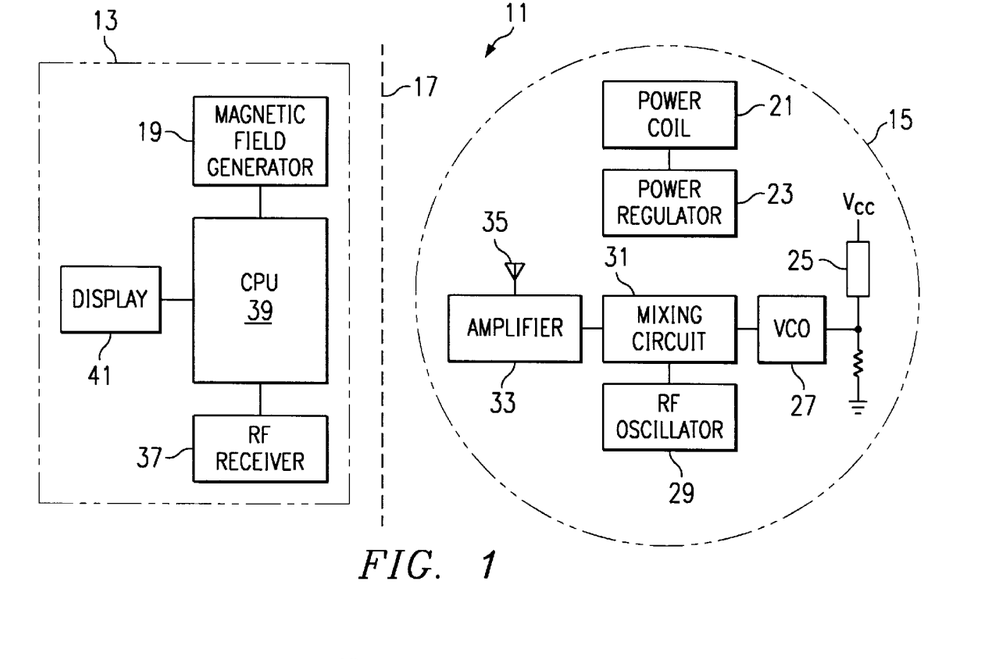
FIG. 1 illustrates a block diagram of a system according to a disclosed embodiment.

Referring now to FIG. 1, there is illustrated a block diagram of a temperature monitoring system according to a disclosed embodiment. A system 11 includes a monitoring unit or station 13 and a temperature sensing transponder 15. Transponder 15 is a small, relatively inexpensive device that is adapted to be placed within the body of a patient or subject. Transponder 15 may be placed either by ingesting, implanting, or injecting. In the disclosed embodiment, transponder 15 is ingested, and it measures and reports the patient's temperature while it passes through the patient's digestive tract, until it is eliminated in the patient's feces. Transponder 15 may also be implanted or injected into the patient's body or a structure within the body to measure temperature over a longer period of time, or to measure the temperature of a particular structure in the body during treatment. The surface of the patient's body is indicated schematically by dashed line 17 with the interior of the body to the right of line 17 and the exterior to the left.

In the embodiment of FIG. 1, transponder 15 is functionally a passive transponder of the type disclosed generally in the following patents: Carroll et al., U.S. Pat. No. 5,347,263, entitled "Electronic Identifier Apparatus And Method Utilizing A Single Chip Microcontroller And An Antenna Coil," issued Sep. 13, 1994; Urbas et al., U.S. Pat. No. 5,252,962, entitled "System Monitoring Programmable Implantable Transponder," issued Oct. 12, 1993; Carroll, U.S. Pat. No. 4,857,893, entitled Single Chip Transponder Device," issued Aug. 15, 1989; and Hoover, U.S. Pat. No. 4,345,253, entitled "Passive Sensing And Encoding Transponder," issued Aug. 17, 1982; the disclosures of which are incorporated herein by reference. Passive transponders do not include an on-board power source such as a battery. Rather, passive transponders receive power from an external source, typically through an inductive link.

The monitoring station 13 includes a magnetic field generator 19 which directs low-frequency electromagnetic radiation at the patient's body, and transponder 15 located therein. The low-frequency electromagnetic radiation generated by magnetic field generator 19 induces a current in a power coil 21 carried by transponder 15. A power regulator 23 rectifies and regulates the current induced in power coil 21 to provide a relatively constant DC voltage level of about three volts to the circuitry of transponder 15.

Transponder 15 includes a temperature sensor 25, which in one embodiment is a thermistor and in another embodiment is an internal temperature reference. As is known to those skilled in the art, a thermistor is a resistive circuit component having a high negative temperature coefficient of resistance. While a thermistor is the preferred temperature sensor, those skilled in the art will recognize that other semiconductor temperature sensing technologies can be incorporated into the transponder of the present invention. For example, temperature sensors 25 of the type are disclosed in the following patents may be used: Gambino et al., U.S. Pat. No. 5,154,514, entitled "On-chip Temperature Sensor Utilizing A Schottky Barrier Diode Structure," issued Oct. 13, 1992, or Rupp U.S. Pat. No. 5,821,599, entitled "Temperature Sensor Having A P-N Junction," issued Oct. 13, 1998, the disclosures of which are incorporated herein by reference.

Temperature sensor 25 produces a voltage that is input to a voltage controlled oscillator 27. Voltage controlled oscillator 27 produces a signal, the frequency of which is related to the input voltage. Thus, the frequency of the signal produced by voltage controlled oscillator 27 is related to the temperature sensed by temperature sensor 25. The signal produced by voltage controlled oscillator 27 modulates a radio frequency (RF) signal produced by an RF oscillator 29. The modulation occurs in a mixing circuit 31. The modulated output from mixing circuit 31 is output to an RF amplifier 33. The amplifier 33 amplifies the signal and outputs the amplified signal to an antenna 35. Antenna 35 may be a separate antenna carried by transponder 15, or it may be integral with the power coil 21.

Antenna 35 of transponder 15 radiates the temperature-modulated RF signal exterior of the body. The temperature modulated RF signal is received by an RF receiver 37, which is part of monitoring station 13. The RF receiver 37 is a conventional receiver that detects the modulation frequency of the signal received from transponder 15. The RF receiver 37 is coupled to a central processing unit (CPU) 39, which determines the temperature detected by transponder 15 based upon the modulation frequency. Preferably, CPU 39 accesses a look up table that relates frequency to temperature in order to determine the temperature detected by temperature sensor 25.

Monitoring station 13 includes a display 41 connected to CPU 39. Display 41 may be a simple LED (light emitting diode) display that provides simply an indication of current temperature. Alternatively, display 41 may be a video monitor with elaborate graphical features that provide a record of temperature over time, as well as other patient information. Monitoring station 13 may provide audio or visual alarms whenever a temperature outside of a normal range is detected. Monitoring station 13 may be a handheld, wand-like unit that may be swept over the patient's body to read temperature. Alternatively, monitoring station 13 may be a fixed or cart-mounted unit. Additionally, magnetic field generator 19 may be separated physically from the other elements of monitoring station 13. Furthermore, CPU 39 and display 41 may be part of a personnel computer connected to RF receiver 37 through an appropriate interface.

While a disclosed embodiment of transponder 15 operates in an analog mode, those skilled in the art will recognize that a transponder can operate in a digital mode. In a digital mode, the voltage produced by the temperature sensor would be sampled periodically by an A/D converter. The sampled digital values would then be modulated onto an RF carrier.

Figure 2:
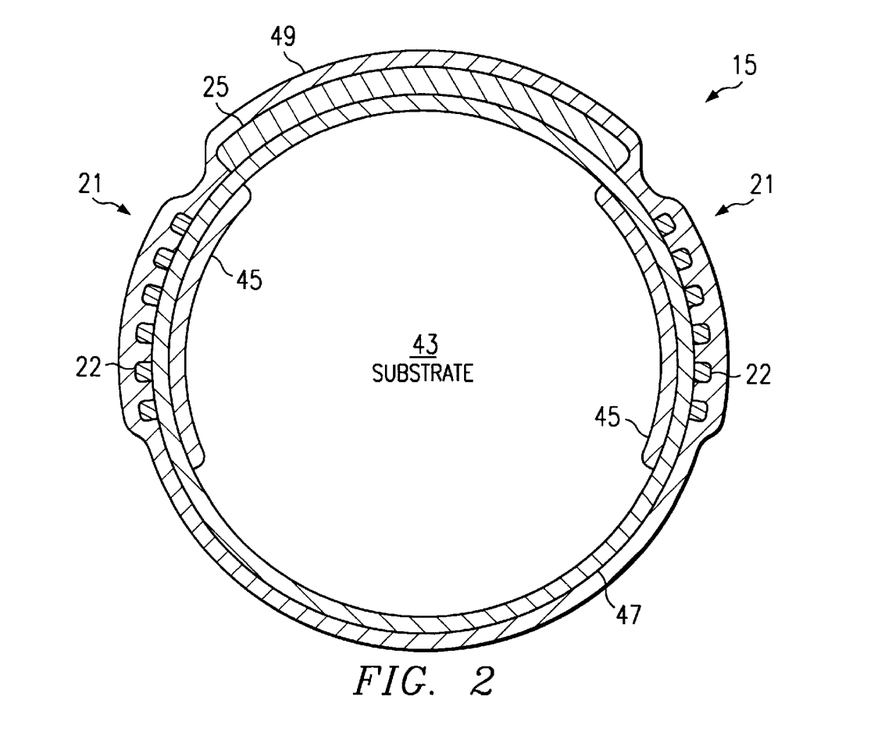
FIG. 2 illustrates a cross section of a temperature transponder according to a disclosed embodiment.

Referring now to FIG. 2, there is illustrated a cross section view of the transponder having the temperature sensor. The transponder 15 preferably comprises a spherical-shaped semiconductor device on which an integrated circuit has been formed. Such a spherical-shaped integrated circuit semiconductor device (sometimes referred to herein as a "ball") is described in commonly assigned U.S. Pat. No. 5,955,776, filed May 16, 1997, issued Sep. 21, 1999, entitled "Spherical-Shaped Semiconductor Integrated Circuit," the disclosure of which is incorporated herein by reference. The transponder 15 is built on a substantially spherical semiconductor substrate 43, which may be doped with P-type or N-type impurities in accordance with the particular requirements of the fabrication process. Semiconductor circuitry, indicated generally at 45, resides on substrate 43. Circuitry 45 includes the power regulator 23, voltage controlled oscillator 27, RF oscillator 29, mixing circuit 31, and amplifier 33, as well as other circuitry. Substrate 43 and circuitry 45 are covered by an insulating layer 47. Insulating layer 47 is preferably formed of silicon dioxide or phosphosilicate glass. The temperature sensor 25 is disposed as the surface of insulating layer 47. Suitable connections are provided through the insulating layer 47 to circuitry 45.

Power coil 21 is formed of helically-wrapped windings over the insulating layer 47. The power coil 21 may have any number of individual windings 22 which can be fabricated from a deposited layer of aluminum that is patterned and etched using conventional semiconductor fabrication techniques. The actual number of individual windings of power coil 21 may be far greater than the six illustrated.

Transponder 15 is coated with or encapsulated in a layer 49 of biologically inert material such as phosphosilicate glass. Coating 49 can withstand the acidity of the stomach to a pH level of about 1.5 and it is not subject to the enzymatic actions in the digestive tract. Transponder 15 is substantially spherical and preferably about one millimeter in diameter. The very small size and round shape facilitates easy swallowing or implantation. However, the device should be made large enough not to be absorbed through the microvilli in the lining of the digestive tract.

Figure 3:
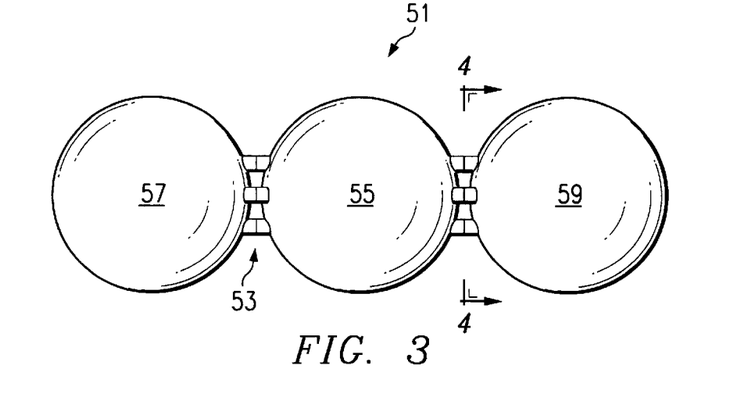
FIG. 3 illustrates a view of the temperature transponder according a disclosed embodiment.

Referring now to FIG. 3, there is illustrated a side view of a three-ball transponder. A transponder 51 comprises three separate balls (55, 57, and 59) interconnected by metallic contact interface 53 comprising one or more contacts or solder bumps. The balls of the transponder 51 include a circuit ball 55, a sensor ball 57, and a battery ball 59. Circuit ball 55 includes a substantially spherical semiconductor substrate upon which resides a least the voltage controlled oscillator 27, RF oscillator 29, mixing circuit 31, and amplifier circuit 33. Sensor ball 57 includes the temperature sensor 25, in this embodiment, which may be a thermistor or a band gap circuit. Battery ball 59 includes a miniature battery that is constructed of non-toxic materials and provides a self-contained DC power source, and which is discussed in greater detail hereinbelow. Transponder 51 is encapsulated in a biologically inert material such as phosphosilicate glass.

Figure 4:
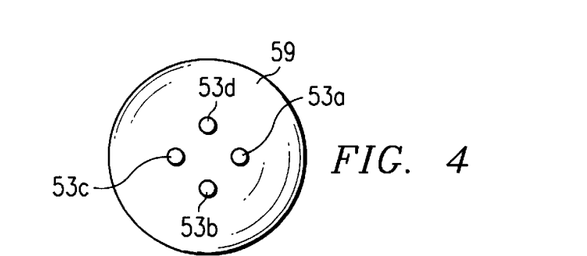
FIG. 4 illustrates a cross section of the metallic contact interface taken along the line 4—4 of FIG. 3 to expose one or more interface contacts.

Referring now to FIG. 4, there is illustrated a cross section of the metallic contact interface taken along the line 4—4 of FIG. 3 to expose, in this example, four contacts, 53a, 53b, 53c and 53d between ball 57 and ball 55. The contacts 53a and 53b may be power contacts, such as a positive 3.0 volts and ground, which can be passed from ball 57 around ball 55 by conductors on its surface using two of a group of similar contacts (designated collectively by numeral 53 in FIG. 3). The contacts 53c and 53d may be data and control contacts for communications between ball 57 and ball 55. Similar data and control contacts may exist among contact group 53 between ball 55 and ball 59 to the extent needed. Although a single transponder 51 can include the foregoing functions, more complex transponder configurations may be constructed having one or more of each of the above mentioned battery ball 59, circuit ball 55, and sensor ball 57 to enable enhanced measurement capabilities of the numerous bodily quantitative conditions such as pH, $pO_2$, $pCO_2$, or temperature, as the particular application requires.

Figure 5:
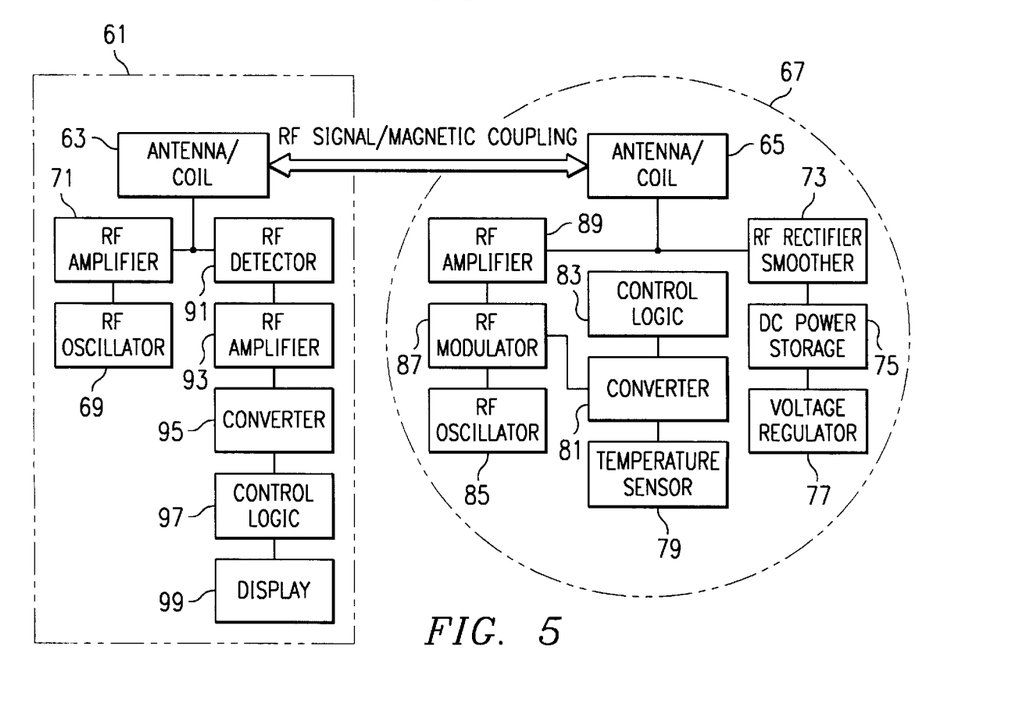
FIG. 5 illustrates an alternative embodiment of the system.

Referring now to FIG. 5, there is illustrated an alternative embodiment of the system. A monitoring unit 61 includes an antenna/coil 63 that transmits RF power to an antenna/coil 65 of ball transponder 67. Power is transported either by RF radiation or by magnetic coupling between the antenna/coil 63 and antenna/coil 65. Monitoring unit 61 generates RF power with an RF oscillator 69 coupled to an RF amplifier 71. RF amplifier 71 is coupled to antenna/coil 63. The RF power received at antenna/coil 65 of transponder 67 is rectified and smoothed by an RF rectifier smoother 73 coupled to the antenna/coil 65. The RF rectifier smoother 73 converts RF energy to a DC voltage. The DC power is stored in a DC power storage unit 75, which may be a capacitor, a battery, or the combination thereof. The capacitor of the DC power storage unit 75 may be included in the smoothing portion of RF rectifier smoother 73. A voltage regulator 77 is coupled to the DC power storage unit 75. The voltage regulator 77 regulates the DC voltage to provide stable voltage for powering the transponder 67 for any condition or distance between monitoring unit 61 and the transponder 67. The voltage regulator 77 supplies DC voltage to all circuits of transponder 67, in a manner well-known to those skilled in the art.

The transponder 67 includes temperature sensor 79 (similar to temperature sensor 25) for measuring the temperature of the desired physical entity. The output of the temperature sensor 79 is converted to a frequency signal by a converter 81. Control logic 83 communicates with the converter 81 for conversion of the measured temperature data. The control logic 83 may be configured to control the activity of all the circuits on transponder 67, though only a connection to converter 81 is shown. The control logic 83 may be microcontroller, a digital signal processor, or any other processor suitable to the size constraints and functions required to be processed.

To transmit information, the transponder 67 includes an RF oscillator 85. The frequency of RF oscillator 85 is preferably not the same as the frequency generated by RF oscillator 69 of control unit 61. The RF signal produced by RF oscillator 85 is modulated with the signal produced by converter 81 in an RF modulator 87. The modulated RF signal is amplified by an RF amplifier 89, which is coupled to antenna/coil 65. The transponder 67 may operate under AM, FM, PM, or any other analog and digital modulation methods. The information transmitted from the transponder 67 is received at antenna coil 63 of monitoring unit 61. The RF signal received at antenna/coil 63 is detected by an RF detector 91 and amplified by an RF amplifier 93. The amplified signal is converted to a digital signal by a converter 95, which is an A/D (analog-to-digital) converter or a demodulator. The converter 95 is coupled to control logic 97, which processes the data received from transponder 67, and controls a display 99 and other electrical circuitry of monitoring unit 61. The display 99 provides visual signaling to a human operator, and may be a simple as an LED, or as complex as a computer display, or it may simply be an interface to other instrumentation equipment.

Figure 6:
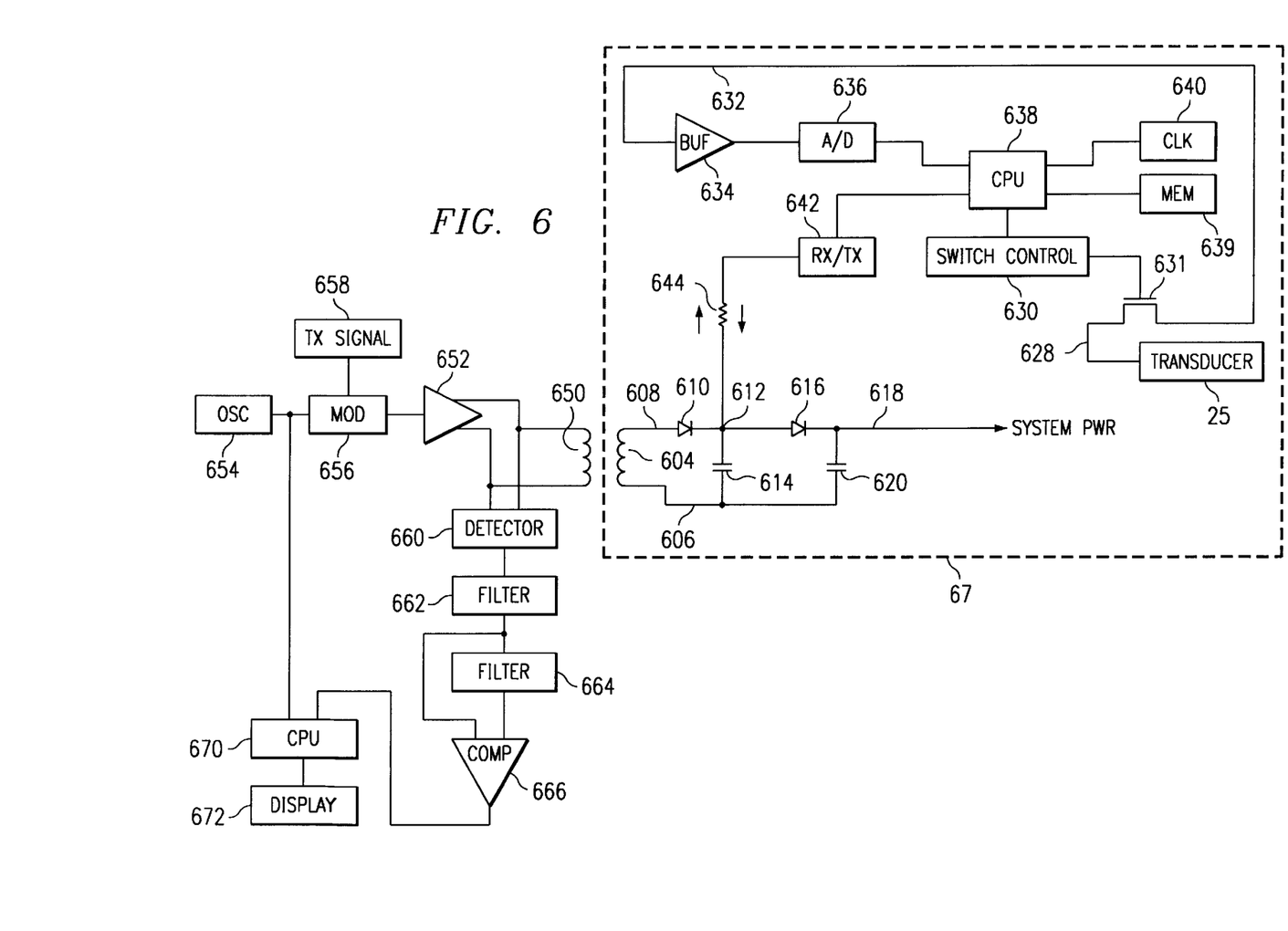
FIG. 6 illustrates a schematic block diagram of the receiver/transmitter and a detection/power system according to a disclosed embodiment.

Referring now to FIG. 6, there is illustrated a schematic block diagram of an alternative embodiment of the monitoring station and transponder of FIG. 5. The transponder 67, as described hereinabove, is operable to provide a sensor 79 for interfacing with the desired quantitive condition. The illustrated alternative embodiment is that associated with a "passive" system, which term refers to a system having no battery associated therewith. In order to operate the system, there is provided an inductive coupling element 604 in the form of an inductor, which is operable to pick up an alternating wave or impulse via inductive coupling, and extract the energy therein for storage in the inductive element 604. This will create a voltage across the inductive element 604 between a node 606 and a node 608. A diode 610 is connected between the node 608 and the node 612, with the anode of diode 610 connected to node 608 and the cathode of diode 610 connected to a node 612. Typically, the diode 610 will be fabricated as a Schottky diode, but can be a simple PN semiconductor diode. For the purposes of this embodiment, the PN diode will be described, although it should be understood that a Schottky diode could easily be fabricated to replace this diode. The reason for utilizing a Schottky diode is that the Schottky diode has a lower voltage drop in the forward conducting direction.

The diode 610 is operable to rectify the voltage across the inductive element 604 onto the node 612, which has a capacitor 614 disposed between node 612 and node 606. Node 612 is also connected through a diode 616 having the anode thereof connected to node 612 and the cathode thereof connected to a node 618 to charge up a capacitor 620 disposed between node 618 and 606. The capacitor 620 is the power supply capacitor for providing power to the transponder 67. The capacitor 614, as will be described hereinbelow, is operable to be discharged during operation of the system and, therefore, a separate capacitor, the capacitor 620, is required for storing power to power the system of the transponder 67.

There is also provided a switching transistor 631 which has one side of the gate/source path thereof connected to a node 628 which is the output of the sensor 79 and the other side thereof connected to a node 632. The gate of transistor 631 is connected to the output of the switch control 630. Node 632 is connected to the input of a buffer 634 to generate an analog signal output thereof which is then converted with an analog-to-digital converter 636 to a digital value for input to a CPU 638. The CPU 638 is operable to receive and process this digital input voltage. A clock circuit 640 is provided for providing timing to the system. A memory 639 is provided in communication with the CPU 638 to allow the CPU 638 to store data therein for later transmittal back to the remote location or for even storing received instructions. This memory 639 can be volatile or it can be non-volatile, such as a ROM. For the volatile configuration, of course, this will lose all information when the power is removed. The CPU 638 is operable to provide control signals to the switch control 630 for turning on the transistor 631 at the appropriate time. In addition to the transistor 631 being toggled to read the sensor 79, transistor 631 could be a pass-through circuit such that the CPU 638 can continually monitor the voltage at the output of the sensor 79. System power to all power-consuming elements of the transponder 67 is provided at the SYSTEM PWR output node.

The memory 639, in conjunction with the operation of the CPU 638, can be operated such that a temperature history can be stored for the internal thermometer. For example, if the internal thermometer in the form of the sensor 67 were ingested and passed through the gut, a temperature history could be recorded at set times. This would require a time base, which is provided by RF oscillator 85 and which would comprise an integral part of the CPU 638 in the embodiment of FIG. 6. This allows information in the form of temperature measurements to be taken at certain times. Once the sensor 67 is eliminated, in one embodiment, it can then be "scanned" and the information stored therein downloaded. Further, this temperature information may only be stored temporarily until a download operation, at which time the memory is cleared and new data is taken. This would allow the memory 639, which may be limited in capacity, to be cleared periodically.

In order to communicate with the CPU 638 for transferring data thereto and for allowing the CPU 638 to transfer data therefrom, a receive/transmit circuit 642 is provided for interfacing to node 612 through a resistive element 644. This allows RF energy to be transmitted to node 612. It is important to note that the semiconductor junction across diode 610 is a capacitive junction. Therefore, this will allow coupling from node 612 to node 608. Although not illustrated, this could actually be a tuned circuit, by selecting the value of the capacitance inherent in the design of the diode 610. In any event, this allows an RF connection to be provided across diode 610 while allowing sufficient energy to be input across inductive element 604 to provide a voltage thereacross for rectification by the diode 610 and capacitor 614. Typically, the frequency of this connection will be in the MHz range, depending upon the design. However, many designs could be utilized. Some of these are illustrated in Beigel, U.S. Pat. No. 4,333,072, entitled "Identification Device," issued Jun. 1, 1982, and Mogi et al., U.S. Pat. No. 3,944,982, entitled "Remote Control System For Electric Apparatus," issued Mar. 16, 1976, which are incorporated herein by reference. With these types of systems, power can continually be provided to the node 612 and subsequently to capacitor 620 to allow power to be constantly applied to the transponder 67.

The monitor system 61 which is disposed outside of the body and proximate to the transponder 67 includes an inductive element 650 which is operable to be disposed in an area proximate to the skin, yet exterior to the body, in the proximity of the transponder 67. The inductive element 650 is driven by a driving circuit 652 which provides a differential output that is driven by an oscillator 654. This will be at a predetermined frequency and power level necessary to couple energy from inductive element 650 to inductive element 604. Since this is an external system, the power of the oscillator can be set to a level to account for any losses through the body tissues. To allow information to be transmitted, a modulation circuit 656 is provided which is modulated by a transmitter signal in a block 658 that allows information to be modulated onto the oscillator signal of the oscillator 654, which oscillator signal is essentially a "carrier" signal. However, it should be understood that the information that is transmitted to the transponder 67 could merely be data information, whereas the CPU 638 could operate independent of any transmitted information to provide the temperature output. Alternatively, entire control of the system could be provided by the transmit signal 658 and the information carried thereon, since power must be delivered to the illustrated embodiment due to the lack of any independent power in the transponder 67.

When the information is received from the transponder 67, it is superimposed upon the oscillator signal driving the inductive element 650. This is extracted therefrom via a detector 660 which has the output thereof input to a first low pass filter 662, and then to a second low pass filter 664. The output of low pass filters 662 and 664 are compared using a comparator 666 to provide the data. The filter 662 provides an average voltage output, whereas the filter 664 provides the actual digital voltage output. The output of the comparator 666 is then input to a CPU 670 which also is powered by the oscillator 654 to process the data received therefrom. This can then be input to a display 672.

Figure 7A:
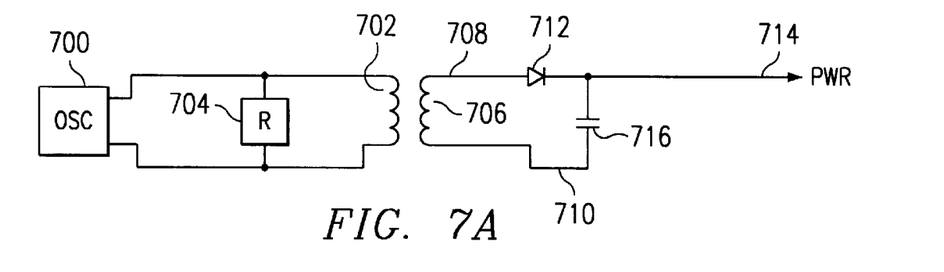
FIGS. 7A–7C illustrate alternative embodiments for the receiver/transmitter and the storage capacitors associated therewith.
Figure 7B:
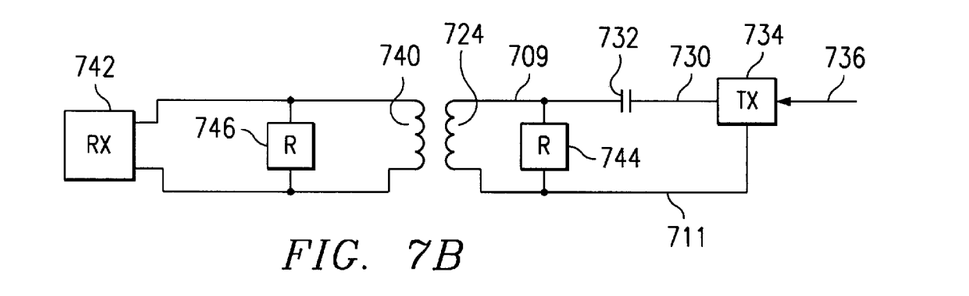
Figure 7C:
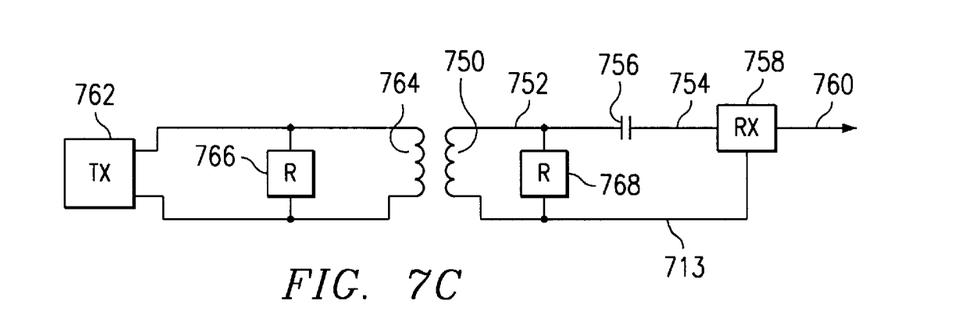

Referring now to FIGS. 7A–7C, there are illustrated alternate embodiments for the transmit/receive operation. In FIG. 7A, there is provided an oscillator 700 which drives an external inductive element 702. Typically, there is some type of load 704 disposed across the inductive element 702. This is the primary power that is provided to the system. A separate inductive element 706 is provided on the transponder 67, for being inductively coupled to the inductive element 702. Thereafter, a voltage is generated across the inductive element 706, the inductive element 706 being connected between nodes 708 and 710. A diode 712 is connected between node 708 and a power node 714, and a power supply capacitor 716 is disposed across node 714 and a node 710. This allows the voltage on node 708 to be rectified with diode 712.

In FIG. 7B, the receive operation, in this alternative embodiment, utilizes a separate inductive element or antenna 724 in the transponder 67, which is operable to be connected between nodes 709 and 711. Node 709 is capacitively coupled to a transmit node 730 with a capacitor 732, the capacitor 732 being a coupling capacitor. A transmitter 734 is provided for transmitting received data from a line 736 to the node 730, which is then coupled to the node 709 to impress the RF signal across the inductive element 724.

A corresponding inductive element 740 is disposed on the external remote controller of remote monitor location 61, which inductive element 740 is operable to be disposed proximate to the inductive element 724, but external to the human body. The inductive element 740 is basically a "pick-up" element which is operable to receive information and function as an antenna, and provide the received signal to a receiver 742. The structure of FIG. 7B is a separate structure, such that node 709 is isolated from node 708, the power receiving node. However, it should be understood that any harmonics of the oscillator 700 would, of course, leak over into the inductive element 724. This can be tuned out with the use of some type of tuning element 744 on the transponder 67 disposed across inductive element 724, and also a tuning element 746 disposed across the inductive element 740, i.e., the antenna.

Referring now to FIG. 7C, there is illustrated a simplified schematic diagram of the receive portion. The transponder 67 has associated therewith a separate receive antenna or inductive element 750 disposed between node 713 and a node 752. Node 752 is capacitively coupled to a receive node 754 with a coupling capacitor 756. A receiver 758 is provided for receiving the information transmitted thereto and providing on the output thereof data on a data line 760. The receiver 758 is operable to receive the RF signal, demodulate the data therefrom, and provide digital data on the output 760. External to the human body and the transponder 67 is a transmitter 762 which is operable to impress a signal across an external inductive element 764. The inductive element 764 basically provides the RF energy and is essentially tuned with a tuning element 766. A corresponding tuning element 768 is provided on the transponder 67 and disposed across inductive element 750, the inductive element 750 acting as an antenna, as well as the inductive element 764.

Note that in circumstances where the signals of transponder 67 cannot be adequately received therefrom and/or power coupled thereto, the external monitor circuitry 61 may need to be inserted into the body proximate to the transponder 67 in order to couple the transmit/receive signals and power. Furthermore, where more than one monitor transponder ball 79 is used, communication of power and data signals between the various monitors 79 may need to employ distinct time periods (i.e., time multiplexing) when communication occurs using a single common frequency, or discrimination circuits may need to be used where communication occurs simultaneously with the plurality of implanted monitors 79 having different oscillator frequencies.

Figure 8:
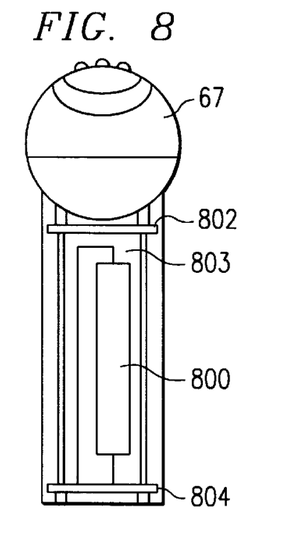
FIG. 8 illustrates a cross-sectional side view of the monitor in an alternate embodiment utilizing a local power source.

Referring now to FIG. 8, there is illustrated a side view of an alternative embodiment utilizing additional circuitry or structure attached to the transponder 67 for providing a local power source. As described hereinabove, the transponder 67 requires a power-generating structure for storing a power supply voltage such that diodes must be provided for receiving and rectifying a large amount of power and charging up a power supply capacitor. Alternatively, the transponder 67 could be configured to interface to an attached power supply system 800 comprising either a battery or a capacitor. The local power supply system 800 is illustrated as disposed on a circuit board 803 defined by supporting structures 802 and 804. The circuit board 803 contains electronics for interfacing the local power supply system 800 to the transponder 67.

Figure 9:
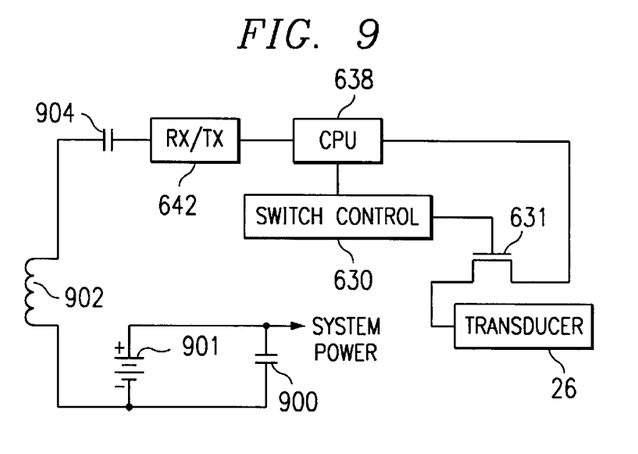
FIG. 9 illustrates a schematic block diagram of the circuitry utilizing a battery as the primary power source.

Referring now to FIG. 9, there is illustrated a schematic block diagram of the transponder 67 using a battery as the local power supply system 800. A battery 901 is provided as a source of self-contained power and is connected across a capacitor 900 to providing smoothing of any power output to the system power-consuming elements of the transponder 67. Power for all on-board components is obtained from the SYSTEM POWER output by providing sufficient charge to the capacitor 900. The capacitor 900 could be formed on the surface of the transponder 67 or it could actually be part of the battery structure 901. Additionally, the capacitance 900 could actually be the capacitance of the battery 901. Additional structure could be provided for powering the CPU 638 and the other circuitry on the transponder 67 from the battery 901. As such, there would only be required a smaller inductive element 902 and a capacitor 904 to allow the receive/transmit block 642 to receive/transmit information from and to the remote exterior monitor station 61. The switch control 630 controls the gate of the switching transistor 631 to switch output of the sensor 79 through the switching transistor 631 source/drain path to the CPU 638.

Figures 10, 11:
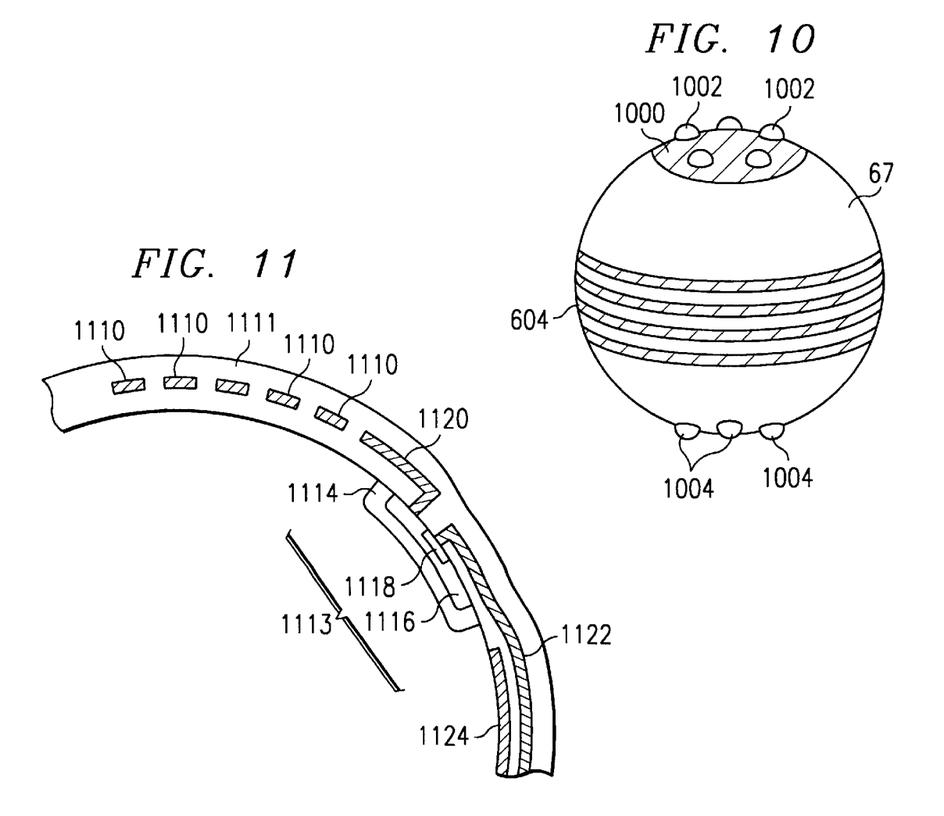
FIG. 10 illustrates a perspective view of one of the spherical semiconductor monitors having the antenna leads disposed thereon.
FIG. 11 illustrates a cross-sectional diagram of the portion of the surface of the spherical monitor ball of FIG. 10.

Referring now to FIG. 10, there is illustrated a perspective view of the transponder 67, wherein the inductive element 604 (inductive element 902 being similar to inductive element 604) is illustrated as being strips of conductive material wrapped around the exterior of the transponder 67. The inductive element 604 is formed of a conductive strip wrapped many times around the transponder 67. The length of inductive element 604 depends upon the receive characteristics that are required. As described hereinabove with reference to FIGS. 7A–7C, there could be multiple conductive strips, each associated with a receive function, a transmit function or a power function, or they could all share one single conductive element or strip. On one end of the transponder 67 there is provided a transducer interface 1000 of the sensor 79 having, optionally, one or more interface balls 1002 (or partial balls, called nodules) associated therewith extending from the transducer interface surface to provide enhanced engagement of the measuring surface or physical entity. The interface balls 1002 can be made of non-reactive material, e.g., gold to prevent degradation while in the body. Note that in some applications, the interface nodules 1002 are not required for obtaining the desired quantitative data. On the other end of the transponder 67 are provided interconnect balls 1004 (or nodules) for interconnecting to one or more other spherical balls which may provide similar functions such as monitoring of quantitative data, or unique functions such as supplying only power or data buffering and storage.

Referring now to FIG. 11, there is illustrated a cross-sectional diagram of the surface of the transponder 67 illustrating the conductive strips forming the inductive element 604. The conductive strips are referred to by reference numeral 1110 which are spaced above the surface of the integrated circuit of the transponder 67 by a predetermined distance, and separated therefrom by a layer of silicon dioxide. A passivation layer 1111 is then disposed over the upper surface of the conductive strips 1110. The conductive strips 1110 can be fabricated from polycrystalline silicon but, it would be preferable to form them from the upper metal layer to result in a higher conductivity strip. This will allow the strips 1110 to be narrower and separated from each other by a larger distance. This separation would reduce the amount of capacitance therebetween.

One end of the strips 1110 is connected to a diode structure 1113. The diode structure 1113 is formed of an N-well implant region 1114 into which a P-well implant region 1116 is disposed, and an N-well implant region 1118 disposed within the P-well implant region 1116. This forms a PN diode where one end of the conductive strips 1110, a conductive connection 1120, is connected to the P-well 1116 implant region, and a conductive layer 1122 is connected at one end to the N-well implant region 1118. This conductive layer or strip 1122 extends outward to other circuitry on the integrated circuit and can actually form the capacitor. Since it needs to go to a capacitor directly, a lower plate 1124 formed of a layer of polycrystalline silicon or metal in a double-metal process, could be provided separated therefrom by a layer of oxide.

Figure 12A:
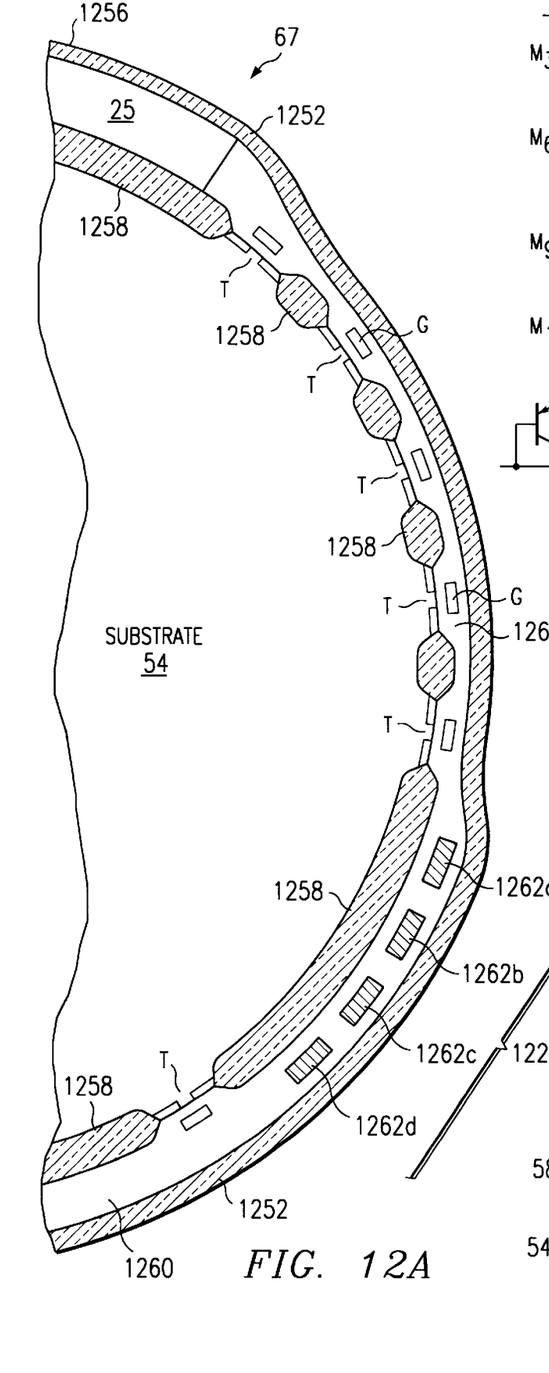
FIG. 12A illustrates additional details of the transponder.

Referring now to FIG. 12A, there are illustrated additional details of the transponder 67. The transponder 67 is hermetically protected by a thin exterior glass passivation layer 1252, which may be phosphosilicate glass (PSG). The interior of the ball transponder 67 comprises a semiconductor substrate 1254, which may be doped p-type or n-type in accordance with the particular requirements of the fabrication process. Optionally, the substrate 1254 may be connected to a stent or other metallic intraluminal device to serve as a ground potential for the transponder 67. The transducer 25 has an outer surface 1256 that is exposed to the bloodstream flowing through the patient's artery (or to any other application which interfaces with fluids flowing in a body lumen). The transducer 25 preferably is formed atop a thick dielectric layer 1258, which may be a field oxide layer grown on the substrate 1254.

A large number of transistors make up the circuitry of the voltage regulator 77, control logic 83 and RF amplifier 89, described above in connection with FIG. 5. Some of these transistors are depicted in FIG. 12A, and labeled with the letter "T." Although these transistors T are schematically depicted as MOS transistors, the integrated circuitry of the transponder 67 could also use bipolar transistors. The individual transistors T are shown separated by portions of the field oxide 1258. Transistor gates G and circuit interconnections (not shown) are embedded in an inter-level dielectric layer 1260 and are made using conventional semiconductor fabrication techniques adapted to the spherical surface of the transponder 67.

The antenna coil 65 described in connection with FIG. 5, is shown as having a plurality of separate windings 1262a, 1262b, 1262c and 1262d, which may be fabricated from a deposited layer of aluminum (or copper) that is patterned and etched using conventional semiconductor fabrication techniques adapted to the spherical shape of the transponder 67. The windings are insulated from each other by portions of the inter-level dielectric layer 1260. The actual number of individual windings of the coil may be far greater than the four specific windings shown. The ends of the coil 65 are connected by additional conductors (not shown) to other circuit elements of the transponder 67.

Figure 12B:
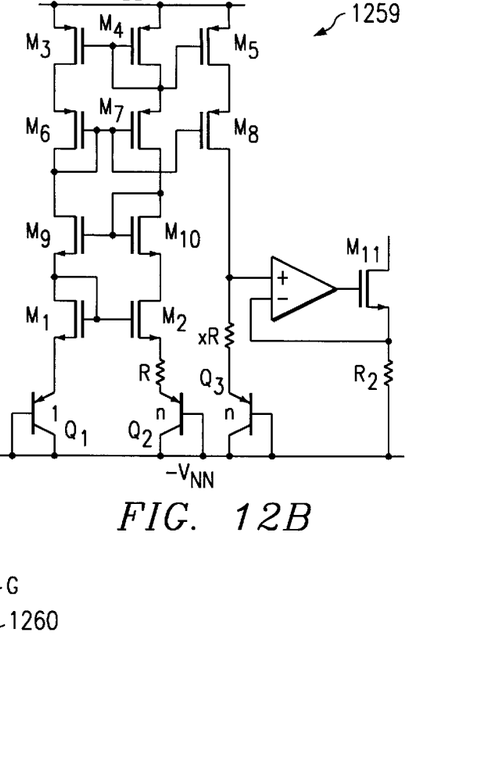
FIG. 12B illustrates a circuit diagram of a temperature compensated current source for use with the transponder.

Referring now to FIG. 12B, there is illustrated a schematic diagram of a temperature compensated current source. The current source is comprised of two legs. The first leg has disposed between a positive and negative rail four MOS transistors and a bipolar transistor. The first MOS transistor is a P-channel transistor labeled $M_3$ having a source/drain path connected between a positive rail and the source-drain path of a P-channel transistor $M_6$. The other side of the source/drain path of transistor $M_6$ is connected to the gate thereof and also to the one side of the source/drain path N-channel transistor $M_9$, the other side thereof connected to one side of the source/drain path of an N-channel transistor $M_1$, and also to the gate of transistor $M_1$. The other side of the source/drain path of transistor $M_1$ is connected to the emitter of a P-channel transistor $Q_1$. The base end collector of transistor $Q_1$ are connected to the ground terminal. The other leg of the current source has a P-channel transistor $M_4$ with one side of the source/drain path thereof connected to the positive rail, the other side thereof connected to one side of the source/drain path of a P-drain transistor $M_7$ and also to the gate of transistor $M_4$ and the gate of transistor $M_3$.

The other side of the source/drain path of transistor $M_7$ is connected to one side of the source/drain of N-channel transistor $M_{10}$ and also to the gate of transistor $M_7$ and the gate of transistor $M_6$, and also to the gate of transistor $M_{10}$. The other side of the source/drain path of transistor $M_{10}$ is connected to one side of the source/drain path of an N-channel transistor $M_2$, the gate thereof connected to the gate of transistor $M_1$ [the gate of transistor $M_{10}$ connected to the gate of transistor $M_9$ and the gate of transistor $M_7$ connected to the gate of transistor $M_6$.] The gate of transistor $M_2$ is connected to the gate of transistor $M_1$. The other side of the source/drain path thereof is connected to one side of a resistor R. The other side of resistor R is connected to the emitter of a PNP transistor $Q_2$, the base end collected thereof connected to ground. The transistors $M_1$–$M_4$, $M_7$ and the bipolar transistors $Q_1$ and $Q_2$ form a conventional supply independent current by a circuit. The leg associated with transistor $QS_1$ provides the reference link with the current source and the transistors associated leg in bipolar transistor $Q_2$ provide the function of the mere leg.

The current through transistor $M_4$ is utilized to generate a bias voltage on the gate of transistor $M_3$ to control a current therethrough. Therefore, the current through transistor $M_4$ is essentially reflected over to transistor $M_3$ such that the current through transistor $M_3$ is equal to the current through transistor $M_4$. The transistors $M_1$ and $M_2$ allow a voltage on the emitter of transistor $Q_1$ to be reflected over to the top of resistor R such that the voltage on the emitter of transistor $Q_1$ and the voltage on the top of resistor R are substantially equal. The current through resistor R generates a voltage $\Delta V_{BE}$ thereacross, which represents the difference in the base-mineral voltages of the two transistors $Q_1$ and $Q_2$. Although the current is equal through both base-emitter junctions of transistors $Q_1$ and $Q_2$, there is a small difference in the base-mineral voltage, this being the voltage developed across the resistor R, this being a Temperature Proportional to Absolute Temperature (TPAT). This current is subtracted from a temperature stable current to therefore provide an offset current. This offset current is inversely proportional to temperature.

The gates of transistors $M_3$ and $M_6$ are output to two series connected P-channel transistors $M_8$ and $M_5$, respectively, disposed between the positive supply and the positive input of a unit gain amplifier. This positive input is also connected to one side of a bias resistor, the other side of which is connected to the emitter of a PNP transistor $Q_3$, the base end collected thereof connected to ground. The output of the amplifier is connected to the gate of N-channel transistor $M_{11}$, the drain thereof connected to the negative input of the amplifier and also to one side of an output load resistor $R_2$ connected on the other side thereof to ground. The source of transistor $M_{11}$ provides a voltage output, which constitutes a temperature dependent voltage.

Figure 12C:
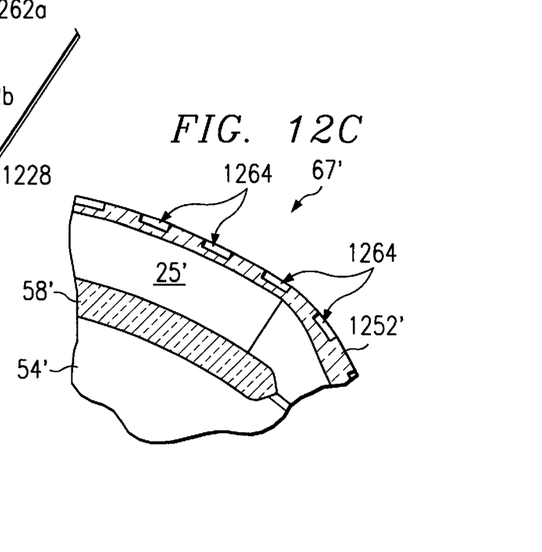
FIG. 12C illustrates a portion of a transponder, as modified from the embodiment of FIG. 12A, using similar reference numerals which designate similar elements.

Referring now to FIG. 12C, there is illustrated a portion of a transponder 67', as modified from the embodiment of FIG. 12A, using similar reference numerals which designate similar elements. The transponder 67' includes a substrate 1254' on which a thick field oxide 1258' has been grown. Overlying the thick field oxide 1258' is a pressure transducer 25' whose outer surface has been modified in accordance with a disclosed embodiment. The portion of dielectric layer 1252' lying over the transducer 25' has recesses 1264 formed in its outer surface. These recesses 1264 may also extend beyond the edges of the transducer 25' at least so far as the monitor's surfaces may be exposed to the bloodstream.

The purpose of the recesses 1264 is to inhibit tissue adhesion to the surfaces of the transponder 67' that are exposed to the patient's blood. Tissue adhesion is known to occur on the surfaces of implants through the attachment of fibroblasts. This phenomenon is well known and is described in Von Recum et al., "Surface Roughness, Porosity, and Texture as Modifiers of Cellular Adhesion," *Tissue Engineering*, Vol. 2, No. 4, 1996 (available from the Dept. of Bioengineering, Clemson University, Clemson, S.C.). The recesses 1264 are presently preferred to be about one micron deep, three microns wide, and spaced three microns apart in a checkerboard topography. Such recesses can be fabricated by conventional selective etching techniques adapted to the spherical shape of the transponder 67.

Although the preferred embodiment has been described in detail, it should be understood that various changes, substitutions and alterations can be made therein without departing from the spirit and scope of the invention as defined by the appended claims.

What is claimed is:

1. A method of monitoring an internal temperature, which comprises the steps of:

placing an externally powered temperature transponder internally of a body wherein said transponder is formed on a single, substantially spherical semiconductor substrate;

generating electromagnetic radiation externally of the body to power the transponder;

generating an RF signal based upon the temperature of the transponder;

receiving the RF signal; and determining the internal temperature based upon the received modulated RF signal.

2. The method of claim 1, wherein the transponder is approximately one millimeter in diameter.

3. The method of claim 1, wherein the transponder is small enough to be easily ingested.

4. The method of claim 3, wherein the transponder is large enough not to be absorbed through microvilli of a digestive tract.

5. An internal thermometer which comprises:

a semiconductor substrate;

a temperature sensor residing on said substrate;

means residing on said substrate for generating an RF signal corresponding to the temperature sensed by said temperature sensor;

means residing on said substrate for powering circuitry residing on said substrate in response to an external electromagnetic signal; wherein said temperature sensor includes means for producing a voltage corresponding to said temperature; and, said means for generating said RF signal corresponding to said temperature includes a voltage controlled oscillator residing on said substrate and coupled to said temperature sensor.

6. The internal thermometer of claim 5, wherein said means for generating said RF signal corresponding to said temperature sensed by said temperature sensor further comprises:

an RF oscillator residing on said substrate; and, a mixing circuit residing on said substrate, said mixing circuit being coupled to said RF oscillator and said voltage controlled oscillator.

7. The internal thermometer of claim 5, wherein said substrate is substantially spherical.

8. An internal thermometer, comprising:

a temperature sensor;

a circuit ball electrically coupled to said temperature sensor, said circuit ball comprising a substantially spherical substrate and circuitry residing on said substrate for generating an RF signal corresponding to the temperature sensed by said temperature sensor; and, means for powering said RF generating circuitry and said temperature sensor.

9. The internal thermometer of claim 8, wherein said temperature sensor resides on said spherical substrate of said circuit ball.

10. The internal thermometer of claim 8, wherein said temperature sensor is defined by a substantially spherical sensor ball electrically coupled to said circuit ball.

11. The internal thermometer of claim 8, wherein said means for powering said RF generating circuitry and said temperature sensor includes circuitry residing on said sensor ball for generating power in response to an external electromagnetic signal.

* * * * *